US010349909B2

(12) United States Patent
Okerlund et al.

(10) Patent No.: US 10,349,909 B2
(45) Date of Patent: Jul. 16, 2019

(54) SYSTEMS AND METHODS FOR FLOW RATE COMPENSATED ACQUISITION PARAMETERS FOR MEDICAL IMAGING

(71) Applicant: General Electric Company, Schenectady, NY (US)

(72) Inventors: Darin Robert Okerlund, Waukesha, WI (US); Mark Vincent Profio, Waukesha, WI (US); Christine Carol Hammond, Waukesha, WI (US); John Irvin Jackson, Brookfield, WI (US); Judy Marie Graney, Mukwonago, WI (US); Chelsey Amanda Lewis, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 451 days.

(21) Appl. No.: 14/788,033

(22) Filed: Jun. 30, 2015

(65) Prior Publication Data

US 2017/0000440 A1    Jan. 5, 2017

(51) Int. Cl.
  *A61B 6/00*    (2006.01)
  *A61M 5/00*    (2006.01)
  *A61B 6/03*    (2006.01)

(52) U.S. Cl.
  CPC ............ *A61B 6/5217* (2013.01); *A61B 6/032* (2013.01); *A61B 6/481* (2013.01); *A61M 5/007* (2013.01)

(58) Field of Classification Search
  None
  See application file for complete search history.

(56) References Cited

U.S. PATENT DOCUMENTS

| 6,408,201 B1 * | 6/2002 | Foo ................. | A61B 5/055 324/300 |
| 6,879,853 B2 * | 4/2005 | Meaney ............. | A61B 5/055 600/420 |
| 7,006,862 B2 | 2/2006 | Kaufman et al. | |
| 7,613,672 B2 | 11/2009 | West et al. | |
| 7,668,286 B2 | 2/2010 | Tsuyuki et al. | |
| 7,979,378 B2 | 7/2011 | West et al. | |

(Continued)

FOREIGN PATENT DOCUMENTS

JP    2001054519 A    *    2/2001

OTHER PUBLICATIONS

JP2001054519: english translation from Espacnet.*

*Primary Examiner* — Tse W Chen
*Assistant Examiner* — Joanne M Hoffman
(74) *Attorney, Agent, or Firm* — Dean D. Small; The Small Patent Law Group, LLC

(57) ABSTRACT

Systems and methods are provided that acquire image data of a first location of a region of interest (ROI) when located in a field of view of a medical imaging system as a contrast material injected into the ROI passes through the first location. The systems and methods further determine from the image data of the first location when a first contrast metric is reached, and after determining the image data of the first location, position the second location of the ROI in the field of view of the medical imaging system. The systems and methods further acquire image data of the second location as the contrast material passes through the second location, and determine from the image data of the second location when the contrast material reaches a second contrast metric.

20 Claims, 7 Drawing Sheets

(56) References Cited

U.S. PATENT DOCUMENTS

| | | |
|---|---|---|
| 8,175,356 B2 | 5/2012 | Movassaghi et al. |
| 2002/0087069 A1* | 7/2002 | Ho .................. G01R 33/56375 600/415 |
| 2002/0091316 A1* | 7/2002 | Foo ...................... G01R 33/563 600/420 |
| 2003/0153823 A1* | 8/2003 | Geiser .................. G06T 7/0012 600/407 |
| 2004/0101088 A1* | 5/2004 | Sabol ..................... A61B 6/481 378/4 |
| 2006/0224104 A1* | 10/2006 | Ohishi .................. A61M 5/007 604/27 |
| 2011/0263973 A1* | 10/2011 | Bernhardt .............. A61B 6/481 600/431 |
| 2012/0014499 A1 | 1/2012 | Feuerlein et al. |
| 2016/0292382 A1* | 10/2016 | Grady ................ G06F 19/3437 |

* cited by examiner

SYSTEMS AND METHODS FOR FLOW RATE COMPENSATED ACQUISITION PARAMETERS FOR MEDICAL IMAGING

BACKGROUND OF THE INVENTION

The subject matter disclosed herein relates generally to systems and methods for computed tomography (CT) imaging.

In CT imaging, an X-ray source may be rotated around an object of interest (e.g., a patient, organ of a patient) to obtain imaging information. During a clinical scan, X-rays emitted from the X-ray source, attenuated by the object of interest, may be collected or detected by a detector and used to reconstruct a medical image.

The object of interest is injected with a contrast agent (e.g., radiocontrast agent, an ionic contrast agent, a barium sulfate contrast agent, a blood agent) to provide maximum contrast in the imaging information. The clinical scan is preferably performed at locations of the object of interest when the contrast agent has filled the desired locations. For obtaining imaging information of the object of interest for long distances, such as greater than three hundred millimeters, the clinical scan ideally follows the contrast velocity rate of the contrast agent traversing within the object of interest. The contrast velocity rate is dependent on the blood flow rate of the object of interest, which may vary between different objects of interest and/or vary locally within the object of interest. If the clinical scan speed is too fast or too slow with respect to the contrast velocity rate, the scanner can "outrun" the contrast agent or the contrast agent may be depleted, respectively, leading to poor and/or uneven contrast opacification of the resultant image derived from the imaging information. To compensate, a larger contrast volume may be injected in subsequent scans leading to an unnecessary contrast dosage, which may be problematic for the patient.

Recently, to determine the contrast velocity rate, multiple bolus injections of the contrast agent are administered. During each injection, a continual scan is performed at separate locations, respectively, to determine a transit time of the contrast agent from an injection location to the respective location being scanned to determine an arrival time of the contrast agent. Based on the arrival times, a contrast velocity rate is approximated which is incorporated into a scan prescription. However, the multiple injections of the contrast agent and continual scans may be adverse to the health of the patient, such as increased radiation exposure, increased chance of having an adverse reaction to the contrast agent, and/or the like.

Thus, there is a need for ensuring a near-uniform contrast opacification of the resultant medical image without increasing risk to the patient.

BRIEF DESCRIPTION OF THE INVENTION

In one embodiment, a method is provided that may include acquiring image data of a first location of a region of interest (ROI) when located in a field of view of a medical imaging system as a contrast material injected into the ROI passes through the first location. The contrast material successively traverses from the first location to a second location of the ROI. The second location is spaced apart from the first location. The method may also include determining from the image data of the first location when a first contrast metric is reached, and after determining the image data of the first location, positioning the second location of the ROI in the field of view of the medical imaging system. The method may also include acquiring image data of the second location as the contrast material passes through the second location. Further, the method may include determining from the image data of the second location when the contrast material reaches a second contrast metric.

In another embodiment, a medical imaging system is provided. The medical imaging system may include an acquisition unit that includes a computed tomography (CT) detector configured to collect imaging data based on a scan prescription. The medical imaging system may also include a processing unit that includes one or more processors operably coupled to the acquisition unit. The processing unit may be configured to receive image data of a first location of a region of interest (ROD when located in a field of view of the acquisition unit as a contrast material injected into the ROI passes through the first location. The contrast material successively traverses from the first location to a second location of the ROI. The second location being spaced apart from the first location. The processing unit may further be configured to determine from the image data of the first location when a first contrast metric is reached, and after determining the image data of the first location, position the second location of the ROI in the field of view of the CT detector. The processing unit may also be configured to acquire image data of the second location as the contrast material passes through the second location. Further, the processing unit may be configured to determine from the image data of the second location when the contrast material reaches a second contrast metric.

In another embodiment, a tangible and non-transitory computer readable medium is provided. The tangible and non-transitory computer readable medium includes one or more computer software modules configured to direct one or more processors. The tangible and non-transitory computer readable medium may direct the one or more processors to acquire image data of a first location of a region of interest (ROI) when located within a field of view of a medical imaging system as a contrast material injected into the ROI passes through the first location. The contrast material successively traverses from the first location to a second location of the ROI. The second location being spaced apart from the first location. The tangible and non-transitory computer readable medium may also direct the one or more processors to determine from the image data of the first location when a first contrast metric is reached, and after determining the image data of the first location, position the second location of the ROI into the field of view of the medical imaging system. The tangible and non-transitory computer readable medium may also direct the one or more processors to acquire image data of the second location as the contrast material passes through the second location, and determine from the image data of the second location when the contrast material reaches a second contrast metric.

DETAILED DESCRIPTION OF THE INVENTION

Figure 1:
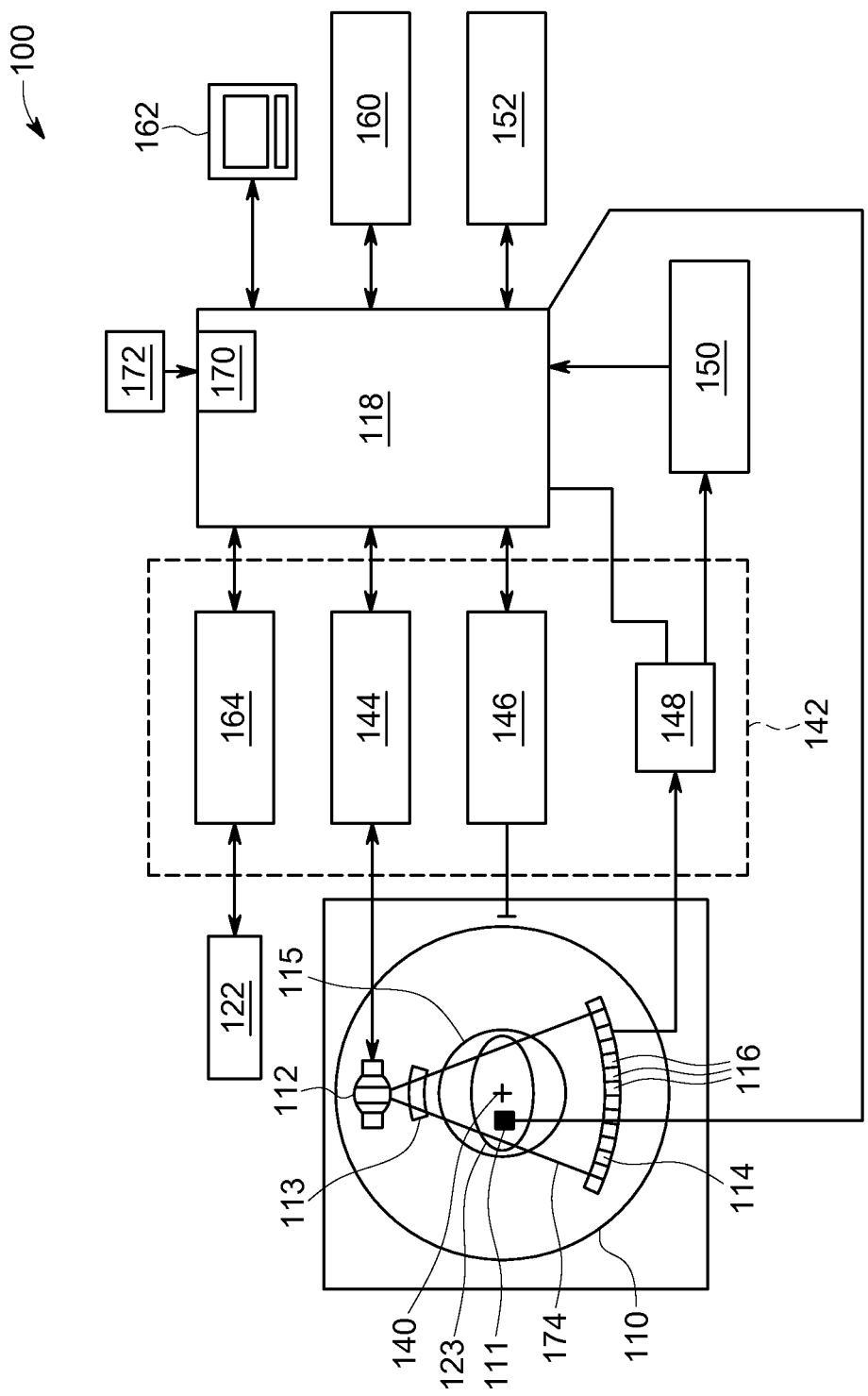
FIG. 1 is a schematic block diagram illustrating an imaging system in accordance with various embodiments described herein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for adaptively determining a select acquisition rate by determining the effective contrast velocity or flow rate in real-time. For example, the contrast at two distinct image locations of a region of interest (ROI) are successively monitored to detect a time of peak enhancement (e.g., contrast agent density) at each location from a single contrast bolus injection. Optionally, one of the two distinct image locations may be a bifurcated segment having first and second branches (e.g., a right leg and left leg). Based on the times of peak enhancement, an average flow rate may be calculated across the two distinct image locations. Optionally, various embodiments may utilize an auto triggering mechanism controlling when X-rays are emitted during the scan. For example, the auto triggering mechanism may be configured to activate an X-ray source at the second distinct image location to avoid emitting X-rays to an object of interest transitioning between the two distinct image locations. Additionally or alternatively, a flow rate report may be displayed on a display based from the determined contrast flow rate. The flow rate report may be a visual representation on the amount of contrast with respect to a position of the ROI.

The flow rate may be utilized to determine optimal acquisition settings corresponding to a scan prescription and reconstruction settings to achieve near-uniform opacification and/or contrast enhancement for CT examinations, and potentially achieving optimal contrast efficiency (e.g., image Hounsfield unit enhancement level per iodine contrast dose). The scan prescription may include one or more select acquisition or scan settings such as the acquisition mode (e.g., step-n-shoot, helical, mixed/variable), parameter settings (e.g., tube current/voltage, focal spot size, duty cycle, kV pair, rotation speed, collimation width, field of view size, body dose, exposure time, head dose, helical pitch, table feed rate), and/or adjustments to the contrast injection protocol (e.g., rate of injection, bolus volume, prep delay) to acquire image information at a speed of the determined contrast flow rate.

Optionally, the two distinct image locations may be determined automatically based on a clinical identification (CID) and patient attributes or characteristics (e.g., size, attenuation, age, heart rate). The CID provides a clinical context and may include an anatomy of interest and a clinical scan identification. Additionally or alternatively, the two distinct image locations may be adjusted by a user (e.g., operator, clinician, doctor) from locations automatically determined by various embodiments and/or identify positions of the two distinct image locations.

A technical effect of various embodiments described herein include an automated work flow to determine a flow rate for acquisition parameters for medical imaging. A technical effect of various embodiments described herein include reducing a number of contrast material injections and scans (e.g., timing bolus acquisition scans) to determine a flow rate of a contrast agent within a region of interest relative to conventional medical imaging systems. A technical effect of the near uniform contrast opacification of various embodiments described herein include improved sensitivity or specificity of advanced vessel luminal analysis during post processing of imaging information acquired from the diagnostic scan.

FIG. 1 illustrates a schematic diagram of an exemplary CT imaging system 100 that may be utilized to implement various embodiment discussed herein. Although the CT imaging system 100 is illustrated as a standalone imaging system, it should be noted that the CT imaging system 100 may form part of a multi-modality imaging system in some embodiments. For example, the multi-modality imaging system may include the CT imaging system 100 and a positron emission tomography (PET) imaging system, or a single photon emission computed tomography (SPECT) imaging system. It should also be understood that other imaging systems capable of performing the functions described herein are contemplated as being used.

The CT imaging system 100 includes a gantry 110 that has the X-ray source 112 that projects a beam of X-rays toward the detector array 114 on the opposite side of the gantry 110. A source collimator 113 and a bowtie filter module (not shown) are provided proximate the X-ray source 112. The detector array 114 includes a plurality of detector elements 116 that are arranged in rows and channels that together sense the projected X-rays that pass through a patient 123 (e.g., object of interest). The imaging system 100 may include a physiologic sensor 111 (e.g., electrocardiogram (ECG), a respiratory sensor) proximate to the patient 123 for cardiac or respiratory gating.

A motorized table 122 is utilized to move the patient 123 into and out of the gantry 110 at a table feed rate. Particularly, the table 122 moves at least a portion of the patient 123 through a gantry opening 115 along a z-axis that extends through the gantry 110. Further, the table 122 may be used to move the patient 123 vertically within the bore of the gantry 110.

The depicted detector array 114 includes a plurality of detector elements 116. Each detector element 116 produces an electrical signal, or output, that represents the intensity of an impinging X-ray beam and hence allows estimation of the attenuation of the beam as it passes through the patient 123. During a scan to acquire the X-ray projection data, the gantry 110 and the components mounted thereon rotate about a center of rotation 140. FIG. 1 shows only a single row of detector elements 116 (i.e., a detector row). However, the multi-slice detector array 114 includes a plurality of parallel detector rows of detector elements 116 such that projection data corresponding to a plurality of slices can be acquired simultaneously during a scan.

In the exemplary embodiment, the X-ray source 112 and the detector array 114 are rotated with the gantry 110 within the imaging plane and around the patient 123 to be imaged such that the angle at which an X-ray beam 174 intersects the patient 123 constantly changes. A group of X-ray attenuation measurements, i.e., projection data, from the detector array 114 at one gantry angle is referred to as a "view" or "projection." A "scan" of the patient 123 comprises a set of views made at different gantry angles, or view angles, during one or more revolutions of the X-ray source 112 and the detector array 114. In a CT scan, the projection data is processed to reconstruct an image that corresponds to a three-dimensional volume taken of the patient 123. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Rotation of the gantry 110, the operation of the X-ray source 112, and position of the motorized table 122 are governed by an acquisition subsystem 142 based on one or more scan settings (e.g., tube current/voltage, focal spot size, duty cycle, kV pair, rotation speed, collimation width, field of view size, body dose, exposure time, head dose, helical pitch) defined by a scan prescription. The acquisition subsystem 142 includes an X-ray controller 144 that provides power and timing signals to the X-ray source 112 based on the scan settings defined by the scan prescription. The X-ray controller 144 may deliver power (e.g., tube current, tube voltage) and/or configure the X-ray source 112 to project X-rays having a certain field of view and/or collimation width (e.g., collimation slab) based on the scan settings defined by the scan prescription. Additionally or alternatively, the X-ray controller 144 may control a focal spot size of the X-ray source 112 based on the scan settings defined by the scan prescription. Optionally, for dual-energy CT scans, the X-ray controller 144 may define the dual energy levels (e.g., kV pair) and duty cycle of the X-rays emitted by the X-ray source 112.

The acquisition subsystem 142 also includes a gantry motor controller 146 that controls the rotational speed and position of the gantry 110. For example, the gantry motor controller 146 may rotate the gantry 110 at a rotational velocity based on the scan settings defined by the scan prescription.

In addition, the acquisition subsystem 142 may also include a table motor controller 164 that controls the motorized table 122 to position the patient 123 in the gantry 110 based on the scan settings defined by the scan prescription. Particularly, the motorized table 122 moves at least a portion of the patient 123 through the gantry opening at a table feed rate.

The scan prescription may be stored on a storage device 152 which is communicatively coupled to the acquisition subsystem 142. The storage device 152 may be a tangible and non-transitory computer readable medium such as flash memory, RAM, ROM, EEPROM, and/or the like. The scan prescription may be defined by a processing unit 118.

The processing unit 118 may include one or more processors. Optionally, the processing unit 118 may include a central controller circuit (CPU), one or more microprocessors, a graphics controller circuit (GPU), or any other electronic component capable of processing inputted data according to specific logical instructions. Additionally or alternatively, the processing unit 118 may execute instructions stored on a tangible and non-transitory computer readable medium (e.g., the storage device 152, integrated memory of the processing unit 118). The processing unit 118 receives the projection data from the detector array 114 and processes the projection data to reconstruct an image of the patient 123.

The processing unit 118 is operably coupled to a display 162 and the user interface 160. The display 162 may include one or more liquid crystal displays (e.g., light emitting diode (LED) backlight), organic light emitting diode (OLED) displays, plasma displays, CRT displays, and/or the like. The display 162 allows the operator to observe the reconstructed image and other data generated by the processing unit 118. For example, the display 162 may display patient information, one or more CT images, components of a display interface, measurements, diagnosis, treatment information, and/or the like.

The user interface 160 controls operations of the CT imaging system 100 and is configured to receive inputs (e.g., CID) from the user. The user interface 160 may include a keyboard, a mouse, a touchpad, one or more physical buttons, and/or the like. Optionally, the display 162 may be a touch screen display, which includes at least a portion of the user interface 142. For example, the user may select one or more user selectable elements shown on the display by touching or making contact with touch sensitive portions of the display 162.

A data acquisition system (DAS) 148 in the acquisition subsystem 142 samples analog data from detector elements 116 and converts the data to digital signals, the projection data, for subsequent processing. An image reconstructor circuit 150 receives the projection data from the DAS 148 and performs an image reconstruction. The image reconstructor circuit 150 may include one or more processors, field programmable arrays, one or more ASICs, a CPU, or any other electronic component capable of processing inputted data according to specific logical instructions. Additionally or alternatively, the image reconstructor circuit 150 may execute programmed instructions stored on a tangible and non-transitory computer readable medium (e.g., the storage device 152, integrated memory of the image reconstructor circuit 150). For example, the one or more processors may perform one or more operations by executing programmed instructions stored on the storage device 152 and/or integrated memory such as EEPROM. The image reconstructor circuit 150 may generate the resultant medical image based on reconstructed settings received via the user interface 160 and/or based on the scan attributes. The reconstruction settings may include select keV energy level(s), iterative reconstruction (e.g., adaptive statistical reconstruction), direct multi-planar reconstruction, algorithmic reconstruction, and/or the like.

The projection data is processed by the image reconstructor circuit 150 to reconstruct resultant medical images that corresponds to a two dimensional (2D) slice taken through the patient 123. The image reconstructor circuit 150 may convert the attenuation measurements associated with the projection data into a medical image of the patient 123. The attenuation measurements are typically converted into units of "CT numbers" or Hounsfield units (HU). The image is represented as a matrix of numbers, with each individual number in the image matrix representing a three-dimensional (3D) volume element in the scanned part, called a "voxel." To obtain a visual image, each voxel is represented as a 2D picture element, or "pixel." Each pixel has a shade of gray based on the HU value representing the attenuation measurement within the corresponding voxel. For example, the HU value may correspond to a brightness of each pixel such that a pixel having a higher HU value may be brighter relative to a pixel having a lower HU value. The reconstructed medical images generated by the image reconstructor circuit 150 are input to the processing unit 118 that stores the image in the storage device 152. Optionally, the image reconstructor circuit 150 may be integrated with and/or similar operations may be performed by the processing unit 118.

Additionally or alternatively, the processing unit 118 includes a device 170, for example, a CD-ROM drive, DVD drive, magnetic optical disk (MOD) device, and/or any other digital device including a network connecting device such as an Ethernet device for reading instructions and/or data from a tangible non-transitory computer-readable medium 172.

Figure 2:
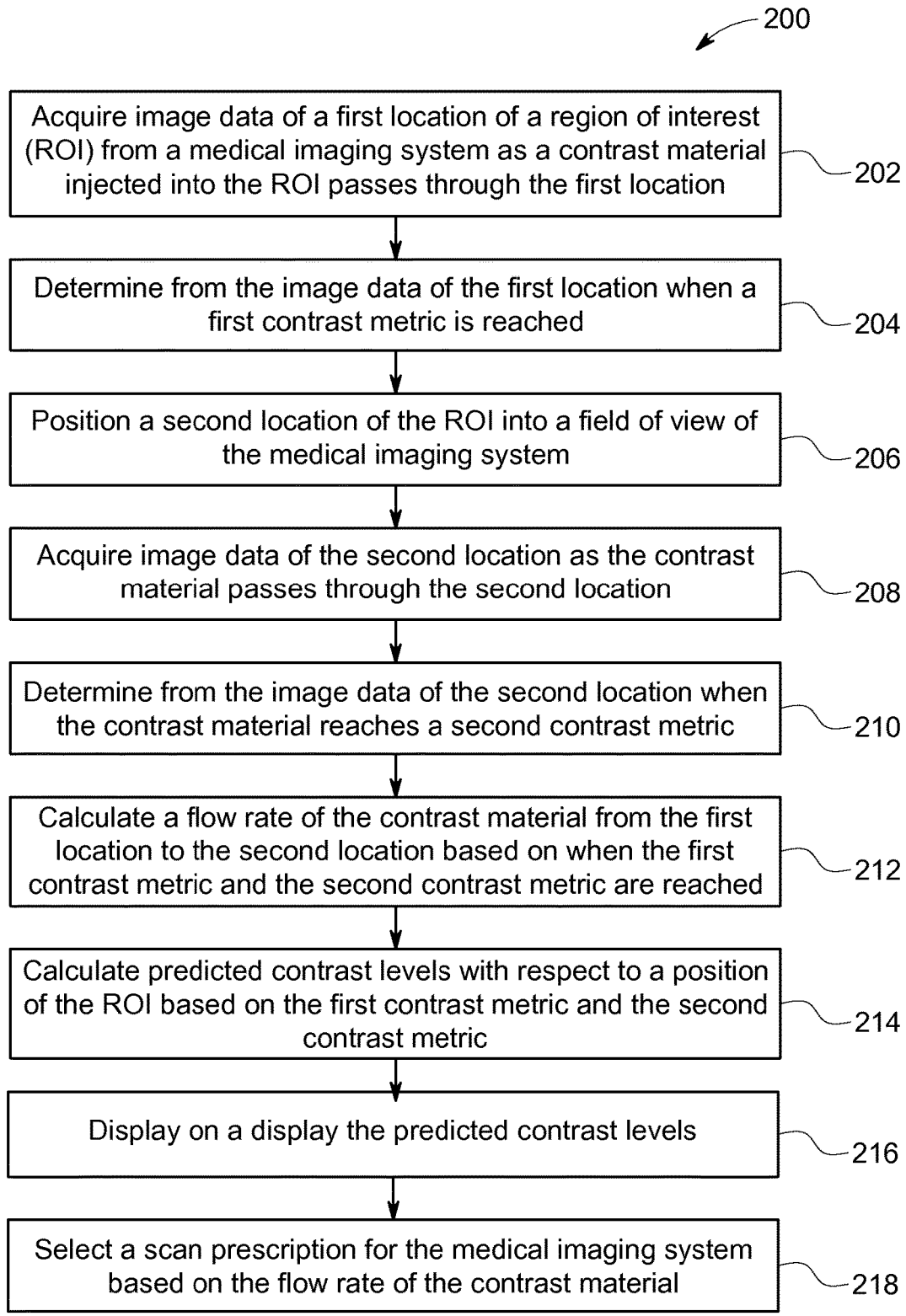
FIG. 2 is a flowchart of a method in accordance with various embodiments described herein.

FIG. 2 illustrates a flowchart of a method 200 for flow rate compensated acquisition parameters for medical imaging. Unless specifically structure is otherwise identified, the operations of FIG. 2 are implemented by one or more processors executing program instructions stored in memory The method 200, for example, may employ structures or aspects of various embodiments (e.g., systems and/or methods) discussed herein, such as the CT imaging system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein. It should be noted, other methods may be used, in accordance with embodiments herein.

One or more methods may (i) acquiring image data of a first location of a region of interest (ROI) from a medical imaging system as a contrast material injected into the ROI passes through the first location; (ii) determine from the image data of the first location when a first contrast metric is reached; (iii) position a second location of the ROI into a field of view of the medical imaging system; (iv) acquire image data of the second location as the contrast material passes through the second location; and (v) determine from the image data of the second location when the contrast material reaches a second contrast metric.

Beginning at 202, image data of a first location of an ROI is acquired from the CT imaging system 100 as a contrast material injected into the ROI passes through the first location. For example, the acquisition system 142 positions the detector array 114 such that the first location of the ROI is located within the field of view associated with the detector array 114. The acquisition subsystem 142 then directs the X-ray source 112 to emit a predetermined dose of radiation, a portion of which is detected at the detector array 114. The contrast material may be a radiocontrast agent, an ionic contrast agent, a barium sulfate contrast agent, a blood agent, and/or the like. For example, the contrast material may be configured to increase the attenuation and/or contrast of the resultant medical image to allow the anatomy (e.g., vascular structure) of the patient 123 be more distinct relative to a resultant medical image acquired without the contrast material. The contrast material may be injected intravenously (IV) into the patient 123 and/or ROI.

The ROI may correspond to an anatomy of interest of the patient 123. For example, the ROI may be one or more organs (e.g., liver, kidney, heart), one or more vascular structure (e.g., aorta), subsections of an organ (e.g., myocardium), and/or the like. The ROI may be selected by the user via the user interface 160 and/or automatically selected by the processing unit 118 as described below. The ROI may extend a length of the patient 123, and correspond to long coverage or range. For example, the ROI may extend from a first edge to a second edge along the Z-axis at greater than (e.g., four hundred millimeters, five hundred millimeters, eight hundred millimeters) and/or equal to three hundred millimeters. In connection with FIG. 3, the ROI 306 may be segmented or subdivided into the first location 302 and a second location 304.

Figure 3:
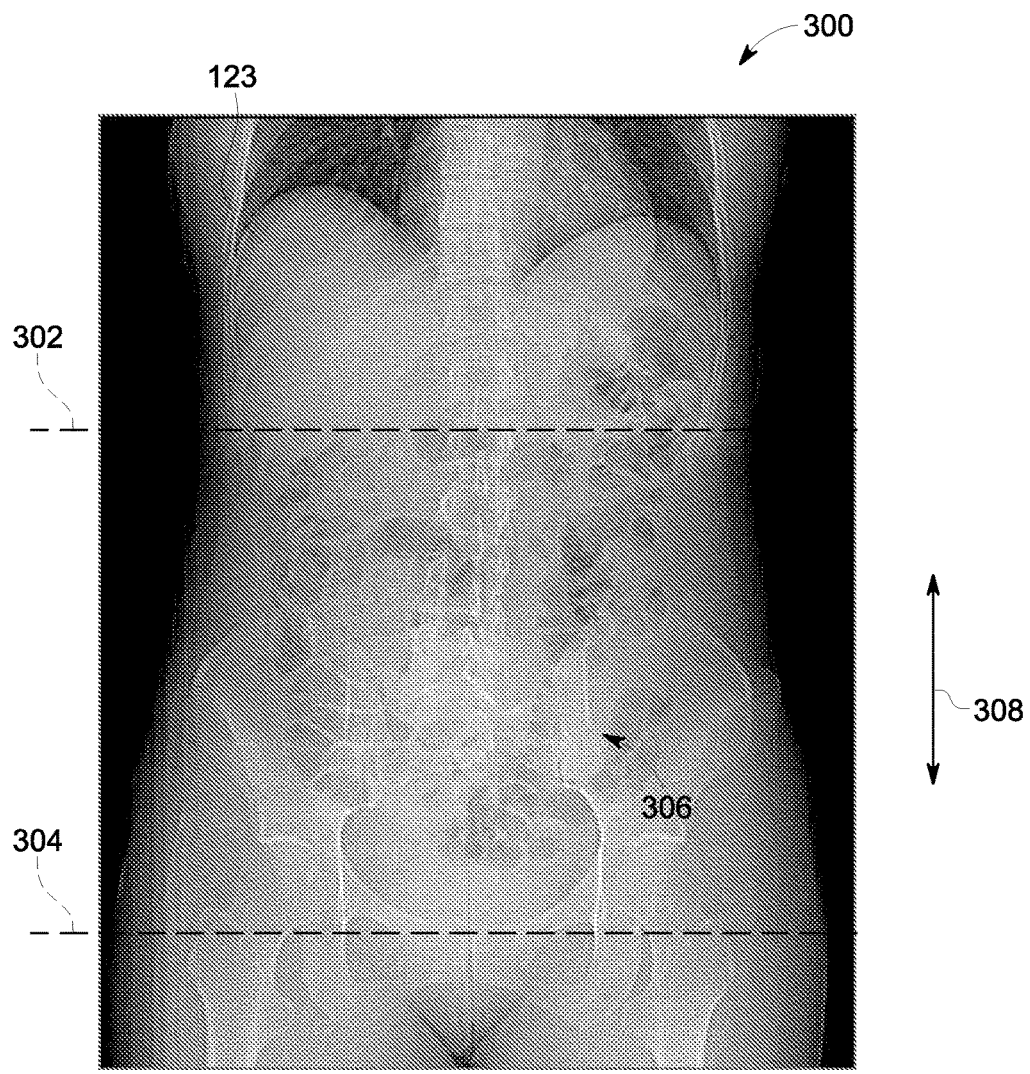
FIG. 3 illustrates a region of interest of a patient having a first location and a second location in accordance with various embodiments described herein.

FIG. 3 is an illustration 300 of the ROI 306 of the patient 123. The ROI 306, as illustrated in FIG. 3, corresponds to an abdomen of the patient 123 which may be associated with an abdominal CT angiography to be performed by the CT imaging system 100 aligned along a Z-axis 308. The first location 302 and/or the second location 304 may be selected by the user via the user interface 160. Additionally or alternatively, the processing unit 118 may automatically determine the first location 302 and/or second location 304 based on the ROI 306.

The second location 304 is spaced apart from the first location 302, which together bound or define the ROI 306 with respect to the patient 123 along the Z-axis 308. For example, the first location 302 may correspond to a first edge of the ROI 306 and the second location 304 may correspond to a second edge of the ROI 306. The first edge and the second edge of the ROI 306 may define and/or be positioned at the boundaries of the ROI 306 along the Z-axis 308. Optionally, the second location 304 may be based on the first location 302. For example, the CT system 100 may have a predefined processing time to reconstruct an image, analyze it, and then move the motorized table 122 to a downstream location (e.g., the second location 302) and start to scan again. Based on the predefined processing time, a minimum distance between the first location 302 and the second location 304 may be defined. Additionally or alternatively, the minimum distance may further be based on a maximum table speed (including acceleration and deceleration times) of the motorized table 122 and/or a maximum expected speed of the contrast flow.

It should be noted in various other embodiments the ROI 306 may be segmented or subdivided into additional locations. For example, the ROI 306 may include a third location interposed between the first location 302 and the second location 304. The third location may be a chest, pelvis, knees, and/or the like.

The first location 302 is positioned to be a leading segment of the ROI 306 such that the contrast material pass through the first location 302 prior to and/or before the second location 304 (e.g., a trailing segment of the ROI 306). The contrast material successively traverses from the first location 302 to the second location 304 of the ROI 306. For example, the first location 302 may be more proximate to the point of injection of the contrast material and/or aspects of the cardiovascular system associated with the ROI 306 relative to the second location 304. As the contrast material is injected into the cardiovascular system, the contrast material may traverse within the vascular structure of the patient 123 and pass through the ROI 306. The first location 302 may be positioned with respect to the ROI 306 such that the contrast material may initially pass through the vascular structure proximate to the first location 302 before passing through the second location 304.

Additionally or alternatively, the ROI 306 and/or the first location 302 and second location 304 may be automatically determined by the processing unit 118 based on a clinical identification (CID) received by the processing unit 118. The CID corresponds to a clinical context for the scan. For example, the CID may include an anatomy interest (e.g., organ of interest, region of interest) of the patient 123 and a clinical indication. The clinical indication may correspond to the purpose or objective of the scan. For example, the clinical indication may correspond to a lesion on the anatomy of interest, a follow-up scan after a medical procedure, an imbedded medical device approximate to the anatomy of interest (e.g., stint), and/or the like.

The CID may be received by the processing unit 118 from the user interface 160. For example, the CID may be selected by the user from a plurality of candidate CIDs displayed on a display interface or graphical user interface (GUI) shown on the display 162. The GUI may include one or more interface components (e.g., a corresponding to user selectable elements shown visually on the display 162, and may be selected, manipulated, and/or activated by the user operating the user interface 160 (e.g., touch screen, keyboard, mouse). The interface components may be presented in varying shapes and colors, such as a graphical or selectable icon, slide bar, and/or the like. Optionally, one or more interface components may include text or symbols, such as a drop-down menu, a menu bar, a title bar, a window (e.g., a pop-up window) and/or the like. Additionally or alternatively, one or more interface components may indicate areas within the GUI for entering or editing information (e.g., CID, patient characteristics) within the GUI, such as a text box, a text field, and/or the like.

Based on the CID, the processing unit 118 may automatically determine the ROI 306 and/or a location of the first location 302 and the second location 304 with respect to the ROI 306. For example, the processing unit 118 may determine the ROI 306, the first location 302, and the second location 304 from the corresponding CID based on a scanning position table. The scanning positioning table may be a collection of candidate positions of interest with respect to the patient 123 with associated CIDs. The scanning positioning table may be stored on storage device 152. Additionally or alternatively, the scanning positioning table may be stored remotely, for example, on a remote server communicatively coupled (e.g., Ethernet, wireless, internet, networked) with the CT imaging system 100. The scanning positioning table may be used as a look up table by the processing unit 118 to match a corresponding CID received by the processing unit 118 with a corresponding position of the patient 123 that may correspond to an ROI, a first location and/or second location. The scanning positioning table may be generated from user inputs from the user interface 160. Optionally, the scanning positioning table may be generated from priori information (pre-programmed rule sets).

Prior to and/or during the injection of the contrast material, the processing unit 118 may instruct the acquisition subsystem 142 to acquire image data of the first location 302 based on one or more acquisition settings generated by the processing unit 118. The one or more acquisition settings may control a position of the motorized table 122 with respect to the gantry 110, rotation speed of the gantry 110, the power and timing settings of the X-ray source 112, and/or the like. For example, the acquisition settings may include a position and/or distance the motorized table 122 may move in order to position the first location 302 into a field of view (FOV) of the X-ray source 112. The acquisition subsystem 142 may reposition the motorized table 122 via the table motor controller 164 based on the acquisition settings.

When the first location 302 is within the FOV of the X-ray source 112, the processing unit 118 may initiate a scan. For example, the X-ray controller 144 may deliver power and timing signals to the X-ray source 112, and the gantry motor controller 146 may rotate the gantry 110 around the patient 123 based on the acquisition settings. The Projection data is acquired from the detector array 114 and received by the processing unit 118, which may convert the projection data into image data. The processing unit 118 may instruct the acquisition subsystem 142 to continually scan the first location 302. From the continual scans, the image data acquired by the processing unit 118 may include a plurality of successive contrast value of the first location 302 over time.

The contrast values may be associated with the amount of contrast material present at the first location 302. For example, as an increased density and/or amount of the contrast material passes through the first location 302, the attenuation of the tissue and/or structures of the first location 302 may increase. The increased attenuation measurements may correspond to an overall increase in CT numbers or HU values of the image data. Likewise, as the density and/or amount of the contrast material passing through the first location 302 decreases, the attenuation and subsequently calculated CT numbers or HU values of the image data decreases.

Returning to FIG. 2, at 204, the processing unit 118 determines from the image data of the first location 302 when a first contrast metric is reached. The first contrast metric may correspond to a peak and/or maximum contrast value selected from the successive contrast values of the image data acquired at the first location 302. For example, in connection with FIG. 4, the processing unit 118 may compare a first contrast value 410 of the plurality of successive contrast values with a second contrast value 412 of the plurality of successive contrast values to determine the maximum contrast value of the first contrast peak 420.

Figure 4:
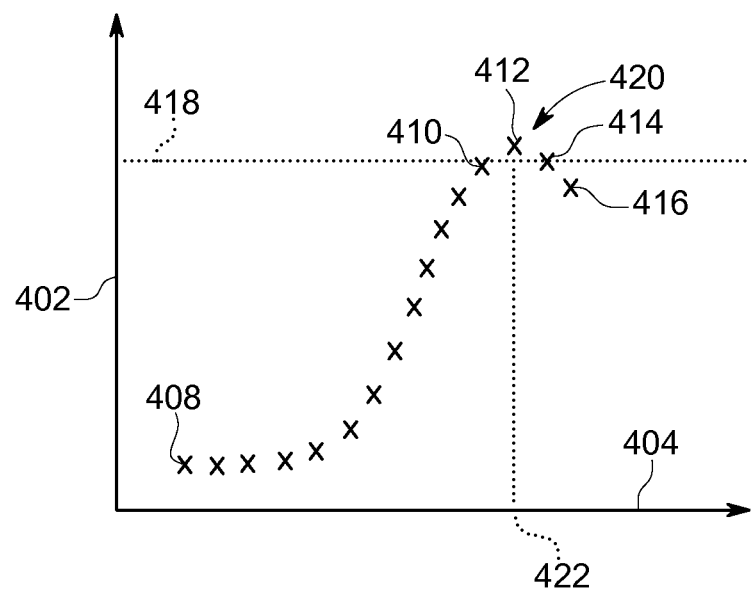
FIG. 4 is a graphical illustration of successive contrast values of image data of a first location in accordance with various embodiments described herein.

FIG. 4 is a graphical illustration of the successive contrast values of the image data acquired at 202. The successive contrast values are composed of contrast values (e.g., 408-416) that are acquired during a corresponding scan, respectively, from the continuous scan described at 202. Optionally, the number of contrast values at a time period may be based on an acquisition rate of the CT imaging system 100. For example, the acquisition rate may be based on an acquisition time corresponding to an amount of time for the processing unit 118 to collect image data for a single scan.

The successive contrast values are shown plotted along a horizontal axis 404 representing time and a vertical axis 402 representing magnitude. The magnitude of the contrast values may correspond to an average HU value of the pixels of the image data acquired during a scan. For example, the contrast value 408 may correspond to an average HU value of the pixels of the image data acquired during a first scan at the first location 302. Additionally or alternatively, the average HU value may not include a portion of the pixels within the image data. For example, the average HU value may not include bright pixels corresponding to bones within the first location 302. Optionally, the magnitude of the contrast values may correspond to a HU value of a select pixel of the image data acquired during a scan.

The processing unit 118 may determine the first contrast peak 420 by sequentially comparing the magnitude of a select contrast value with respect to a previously adjacent contrast value. For example, the processing unit 118 may compare a magnitude of the contrast value 412 with a magnitude of a previous contrast value acquired during the previous or preceding scan, the contrast value 410. The processing unit 118 may determine that since the magnitude of the contrast value 412 is greater than the magnitude of the contrast value 410 the first contrast peak 420 has not been reached, and an additional scan may be performed. The additional scan may acquire the contrast value 414. The processing unit 118 may compare a magnitude of the contrast value 414 with the magnitude of the previous contrast value acquired during the preceding scan, the contrast value 412. The processing unit 118 may determine, since the magnitude of the contrast value 414 is less than the magnitude of the contrast value 412, the first contrast peak 420 has been reached prior to the scan associated with the contrast value 414. The processing unit 118 may determine when the first contrast peak 420 occurred based on when the scan having the corresponding contrast value occurred. For example, the processing unit 118 may determine that the preceding contrast value, the contrast value 412 occurring at 422, which corresponds to when the first contrast peak 420 occurred.

Optionally, the processing unit 118 may perform one or more additional scans to verify that the first contrast peak 420 has been reached. For example, the processing unit 118 may perform an addition scan to acquire the contrast value 416. If the magnitude of the contrast value 416 is less than the magnitude of the contrast value 414 and/or the magnitude of the contrast value 412, the processing unit 118 may determine that the first contrast peak 420 is verified. Alternatively, if the magnitude of the contrast value 416 is greater than the magnitude of the contrast value 414 and/or the magnitude of the contrast value 412, the processing unit 118 may determine that the first contrast peak 420 is not verified and perform additional scans.

Additionally or alternatively, the processing unit 118 may determine the first contrast peak 420 based on descending and/or ascending slopes formed by the successive contrast values. For example, the processing unit 118 may determine the first contrast peak 420 corresponds to a contrast value being interposed between an ascending slope and a descending slope. The slope may represent a ratio of the change in magnitude of the contrast values and the change in time of the scan.

For example, the processing unit 118 may determine an ascending slope from the contrast value 410 to the contrast value 412, and a descending slope from the contrast value 412 to the contrast value 414. Based on the change in magnitude of the slopes from positive to negative, the processing unit 118 may determine that the first contrast peak 420 occurred at and/or near the contrast value 412.

Additionally or alternatively, the processing unit 118 may determine that the first contrast metric is reached when an associated Hounsfield unit (HU) value from the image data of the first location 302 is above a first predetermined threshold 418. For example, the processing unit 118 may compare the contrast value 410 with the first predetermined threshold 418. The processing unit 118 may determine that the magnitude of the contrast value 410 is below the first predetermined threshold 418, and an additional scan may be performed. The additional scan may acquire the contrast value 412. The processing unit 118 may compare the contrast value 412 with the first predetermine threshold 418, and determine that the magnitude of the contrast value 412 is above the first predetermined threshold 418 indicating that the first contrast metric is reached at the contrast value 412 occurring at 422. In various embodiments, the first predetermined threshold 418 may be received by the processing unit 118 from the user via the user interface 160. Additionally or alternatively, the first predetermined threshold 418 may be stored on the storage device 152. Optionally, the processing unit 118 may compare the first contrast peak 420 with the predetermined threshold 418 to verify that the first contrast peak 420 corresponds to the first contrast metric.

Returning to FIG. 2, at 206, the second location 304 (FIG. 3) of the ROI is positioned into a FOV of the medical imaging system. For example, when the first contrast peak 420 is determined at 204, the processing unit 118 may instruct the acquisition system 142, via one or more acquisition settings, to position the second location 304 within the FOV of the X-ray source 112. The acquisition settings may include a position and/or distance the motorized table 122 may move in order to position the second location 304 into the FOV of the X-ray source 112. The acquisition subsystem 142 may reposition the motorized table 122 via the table motor controller 164 based on the acquisition settings.

The positioning operation may be triggered in real-time by the processing unit 118 when the first contrast peak 420 is determined. For example, the motorized table 122 may be repositioned to the second location 304 automatically by the processing unit 118 when the first contrast peak 420 is determined. The real-time triggering provides an automated workflow by advancing from the first location 302 to subsequent locations (e.g., the second location 304) automatically.

Additionally or alternatively, the processing unit 118 may delay repositioning the motorized table 122 to the second location 304 based on a distance between the first location 302 and the second location 304, a feed rate of the motorized table 122, and/or the like.

At 208, image data of the second location 304 is acquired as the contrast material passes through the second location 304. To do so, when the second location 302 is within the FOV of the X-ray source 112, the processing unit 118 may initiate a scan. For example, the X-ray controller 144 may deliver power and timing signals to the X-ray source 112, and the gantry motor controller 146 may rotate the gantry 110 around the patient 123 based on the acquisition settings provided by the processing unit 118. The projection data is acquired from the detector array 114 and received by the processing unit 118, which may convert the projection data into image data. The processing unit 118 may instruct the acquisition subsystem 142 to continually scan the second location 304. From the continual scans, the image data acquired by the processing unit 118 may include a plurality of successive contrast value of the second location 304 over time.

At 210, the method 200 may determine from the image data of the second location 304 when the contrast material reaches a second contrast metric. The second contrast metric may correspond to a peak and/or maximum contrast value selected from the successive contrast values of the image data acquired at the second location 304. The processor 118 may determine the second contrast metric similar to and/or the same as described at 204. For example, the processing unit 118 may compare a first contrast value of the plurality of successive contrast values with a second contrast value of the plurality of successive contrast values to determine the maximum contrast value of a second contrast peak. In another example, the processing unit 118 may determine that the second contrast metric is reached when an associated Hounsfield unit (HU) value from the image data of the second location 304 is above a second predetermined threshold.

The measuring of the contrast material at the second location 304 may be done in real-time by using differences in consecutive images from the image data. The consecutive images may correspond to successive acquisitions by the CT imaging system 100 at the second location 304. Optionally, the measuring of the contrast material be done by comparing the image data with a baseline image. The baseline image may correspond to image data of the second location acquired before the contrast material is injected and/or after the contrast material is through the second location 304. Optionally, the baseline image may correspond to image data acquired during a scout scan.

Optionally, a duration of the scan (e.g., acquisition of image date) at the second location 304 may be determined by a distance between the first location 302 and the second location 304 and a minimum expected average contrast speed. For example, the first location 302 and the second location 304 are separated by 1000 mm. The processing unit 118 may determine that an average contrast flow rate (e.g., contrast speed or velocity) is expected to be in the range of 100 to 500 mm/s. The processing unit 118 may determine that the scan at the second location 304 may not need to continue beyond 10 seconds (e.g., 1000 mm divided by a contrast flow rate of 100 mm/s) after the end of the scanning and/or first contrast metric from the first location 302, since the second contrast metric would have occurred within 10 seconds. Additionally or alternatively, offsets may be used, and a minimum number of scans (e.g., e.g., two scans, three scans) may also be used at the second location 304.

Figure 5:
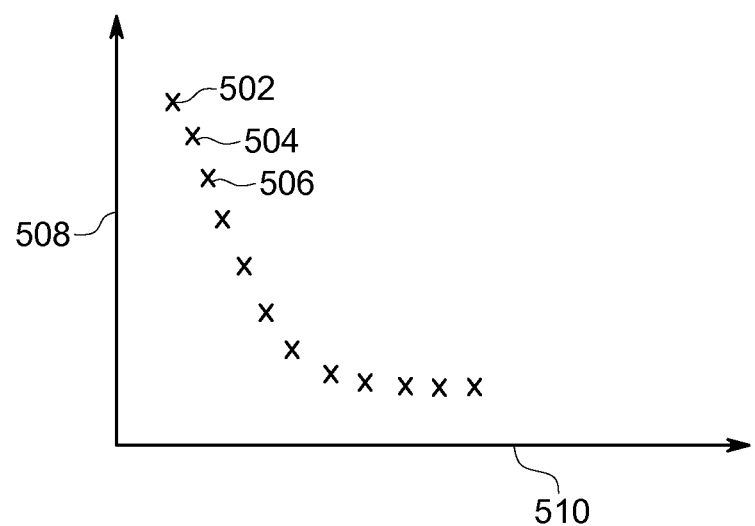
FIG. 5 is a graphical illustration of successive contrast values of image data of a second location in accordance with various embodiments described herein.

Additionally or alternatively, in connection with FIG. 5, the second contrast metric may be determined based on contrast levels occurring subsequent to when the second contrast metric occurred. For example, the processing unit 118 may extrapolate or interpolate when the second contrast metric occurred.

FIG. 5 is a graphical illustration of the successive contrast values of the image data acquired at 208. The successive contrast values are composed of contrast values (e.g., 502-506) that are acquired during a corresponding scan, respectively, from the continuous scan described at 208. The successive contrast values are shown plotted along a horizontal axis 510 representing time and a vertical axis 508 representing magnitude.

As described above, the processing unit 118 may determine the second contrast metric by sequentially comparing the magnitude of a select contrast value with respect to a previously adjacent contrast value. The initial contrast value 502 may correspond to a contrast value acquired during a first scan at the second location 304. The processing unit 118 may compare the initial contrast value 502 with the contrast value 504 acquired subsequent to the first scan. The processing unit 118 may determine that since the magnitude of the contrast value 504 is less than the magnitude of the initial contrast value 502 the second contrast metric occurred at and/or prior to the first scan at the second location 304.

Optionally, the processing unit 118 may perform one or more additional scans to verify that the second contrast metric has occurred. For example, the processing unit 118 may perform an additional scan to acquire the contrast value 506. The processing unit 118 may compare a magnitude of the contrast value 506 with the magnitude of the previous contrast value acquired during the preceding scan, the contrast value 504 and/or 502. The processing unit 118 may determine, since the magnitude of the contrast value 506 is less than the magnitude of the contrast values 502 and/or 504, the second contrast metric has been reached prior to the first scan at the second location 304.

Optionally in various embodiments, the second location may correspond to a bifurcated segment of the ROI. The bifurcated segment may correspond to a portion of the ROI that may be portioned into first and second branches. For example, the bifurcated segment may correspond to a first leg and a second leg of the patient 123. Additionally or alternatively, in connection with FIG. 6, the contrast material may pass through the first branch and the second branch at different rates.

Figure 6:
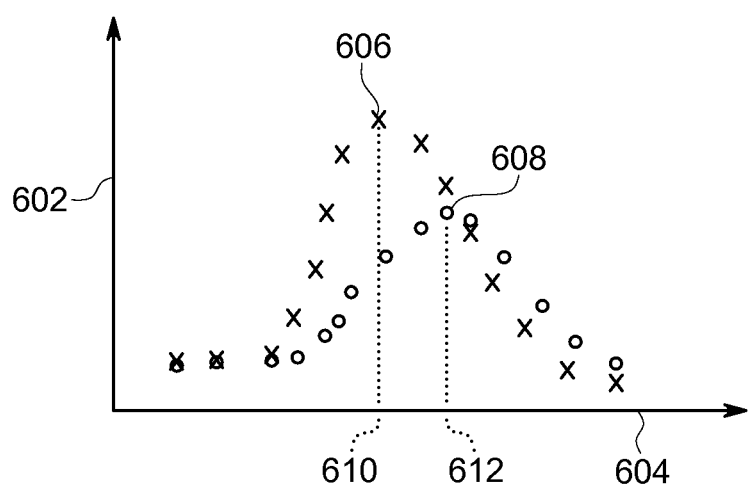
FIG. 6 is a graphical illustration of contrast values from image data of a first branch and a second branch of a bifurcated segment of a second location in accordance with various embodiments described herein.

FIG. 6 is a graphical illustration of the successive contrast values of the image data acquired at 208 from a first branch and a second branch of a bifurcated segment corresponding to the second location 304. The successive contrast values are composed of contrast values (e.g., 606-608) that are acquired during a corresponding scan, respectively, from the continuous scan described at 208. The successive contrast values are shown plotted along a horizontal axis 602 representing time and a vertical axis 604 representing, magnitude. The contrast values acquired from the first branch form the successive contrast values are shown as 'x', and the contrast value acquired from the second branch form the successive contrast value are shown as 'o'.

The processing unit 118 may determine contrast metrics illustrated as contrast peaks 606 and 608 correspond to the first and second branches, respectively, as described above. For example, the processing unit 118 may determine the contrast peak 606 was reached at 610 by sequentially comparing the magnitude of a select contrast value with respect to a previously adjacent contrast value. The contrast material passes through the first and second branches at different rates, for example as illustrated in FIG. 6, the contrast peaks 606 and 608 are reached at different times, at 610 and 612, respectively, thereby the contrast material is passing through the first branch faster than the second branch. Based on the contrast material of the first and second branches, the processing unit 118 may determine the second contrast metric by calculating an average time from the contrast peaks 606 and 608. Additionally or alternatively, the processing unit 118 may select one of the contrast peaks 606 and 608 as the second contrast metric based on a user selection via the user interface 160. It should be noted, that in other embodiments the contrast material may pass through the first branch and the second branch at approximately the same rate.

At 212, a flow rate of the contrast material is calculated by the processing unit 118 from the first location 302 to the second location 304 based on when the first contrast metric and the second contrast metric are reached. The flow rate may correspond to a velocity of the contrast material passing from the first location 302 to the second location 304. For example, the flow rate may be calculated by the processing unit 118 based on a ratio corresponding the time between when the second contrast metric and the first contrast metric 420 are reached divided and/or over the distance between the first location 302 and the second location 304.

It should be noted that the processing unit 118 may determine multiple flow rates between the first location 302 and the second location 304 based on contrast metrics of additional locations interposed between the first location 302 and the second location 304. For example, the processing unit 118 may determine a third contrast metric corresponding to a third location positioned at a midpoint of the ROI 306 between the first location 302 and the second location 304. The processing unit 118 may calculate a first flow rate of the contrast material from the first location 302 to the third location based on when the first contrast metric and the third contrast metric are reached. Additionally, the processing unit 118 may calculate a second flow rate of the contrast material from the third location to the second location 304 based on when the third contrast metric and the second contrast metric are reached.

At 214, the processing unit 118 calculates predicted contrast levels with respect to a position of the ROI based on the first contrast metric and the second contrast metric. The predicted contrast levels may correspond to projected HU image enhancement levels. The processing unit 118 may determine the predicted contrast levels based on the magnitudes or values of the first contrast metric and the second contrast metric corresponding to the first location 302 and the second location 304 of the ROI 306. Optionally, predicted contrast levels may be included in a flow rate report generated by the processing unit 118. The flow rate report may be generated by the processing unit 118 based on the predicted contrast levels and the flow rate of the contrast material. The flow rate report may include the projected contrast levels, the first and second contrast metric values, the successive contrast values form the image data acquired at 202 and 210, and/or the like.

Additionally or alternatively, the processing unit 118 may compare the magnitudes of the first contrast metric and the second contrast metric with a metric target threshold. The metric target threshold may be based on a user input received by the processing unit 118 via the user interface 160. The metric target threshold may correspond to a contrast target level (e.g., density level) for the ROI during the diagnostic scan. The processing unit 118 may determine an adjusted or select volume of the contrast material injected into the patient for the subsequent scan (e.g., diagnostic scan) based on differences between the magnitudes of the metric target threshold with respect to the first contrast metric and/or the second contrast metric, and/or a difference between the first contrast metric and the second contrast metric. The select volume determined by the processing unit 118 may represent an optimized amount of contrast material passing through the ROI 306 to achieve the metric target threshold for the ROI.

For example, if the processing unit 118 determines that that the first contrast metric and/or the second contrast metric is above the metric target threshold the processing unit 118 may determine and/or recommend an acquisition parameter having a select volume of contrast material lower than the contrast volume injected at 202. In another example, if the processing unit 118 determines that the first contrast metric and/or the second contrast metric is below the metric target threshold the processing unit 118 may determine and/or recommend an acquisition parameter having a select volume of contrast material lower than the contrast volume injected at 202.

Figure 7:
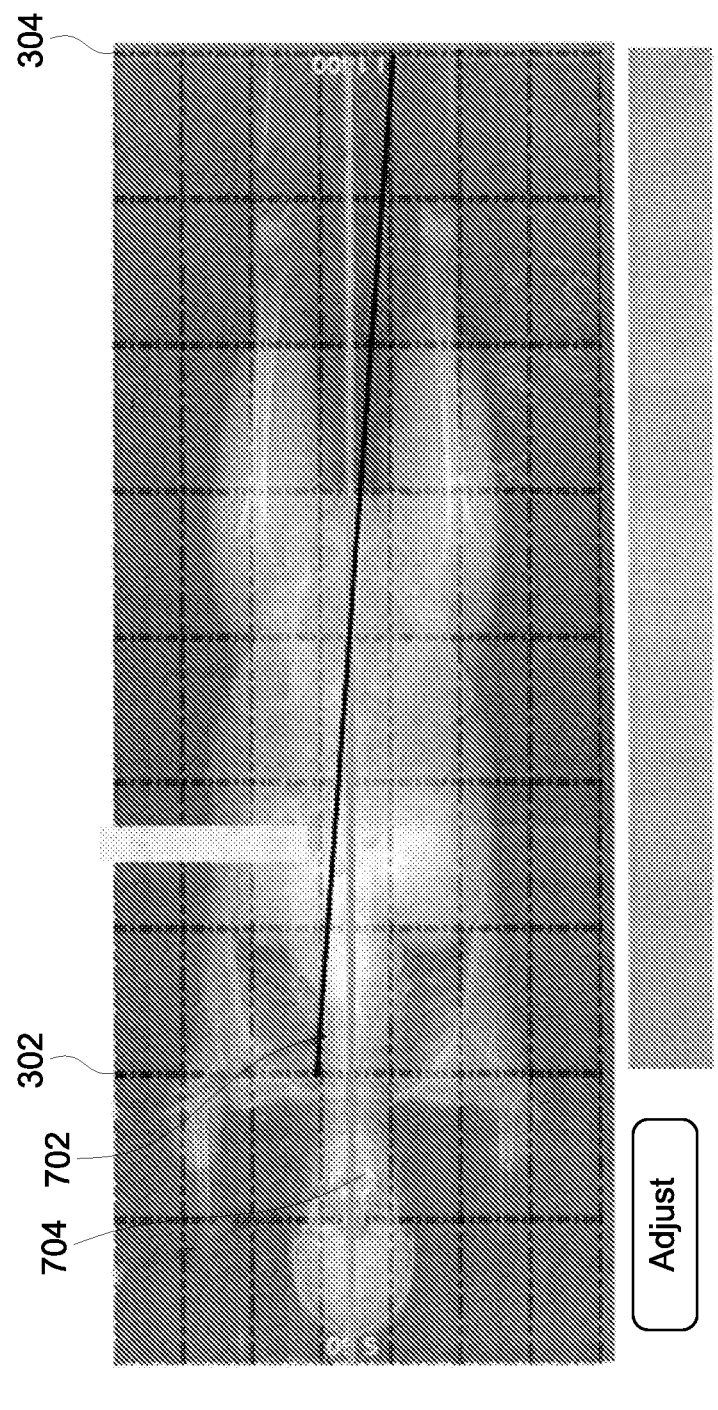
FIG. 7 is an illustration of predicted contrast values in accordance with various embodiments herein.
Figure 7:
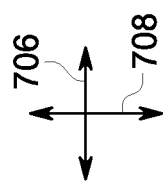

At 216, the predicted contrast levels are displayed on the display 162. FIG. 7 is an illustration of predicted contrast levels forming a curve 702 shown on the display 162 (FIG. 1) extending from the first location 302 to the second location 304. The curve 702 may be overlaid on a generic representation of the patient 123 along a z-axis 706 and a lateral axis 708. The lateral axis 708 may correspond to a magnitude of the predicted contrast level. Additionally or alternatively, the curve 702 may be overlaid on image data obtained during a scout scan.

The curve 702 may be displayed concurrently with a metric target threshold curve 704 representing the metric target threshold. The metric target threshold curve 704 may allow the user to view differences of the curve 702 with respect to the metric target threshold curve 704 at various positions with respect to the ROI 306. For example, as illustrated in FIG. 7, the curve 702 is above the metric target threshold curve 704 at and/or near the first location 302 corresponding to a contrast above the metric target threshold. Additionally, as illustrated in FIG. 7, the curve 702 is below the metric target threshold curve 702 at and/or near the second location 304 corresponding to a contrast below the metric target threshold. Additionally or alternatively, the processing unit 118 may perform a transluminal attenuation gradient (TAG) analysis on structures (e.g., vessel structures) of the ROI 306.

Optionally, at least a portion of the flow rate information, such as from the flow rate report, may be displayed concurrently with the predicted contrast level on the display 162. For example, the HU values (e.g., magnitude of the first contrast metric, magnitude of the second contrast metric) may be shown proximate to and/or overlaid with the curve 702 at the first location 302 and the second location 304. Additionally or alternatively, the flow rate information may be included and/or overlaid on a curved reformat advanced vessel analysis three dimensional rendering shown on the display 162.

Optionally, the user may adjust the flow rate determined by the processing unit 118 via the user interface 160. For example, the user may select, adjust, and/or specify the timing-related values and use the graphic display to see how those timing values will align the flow rate from the first and second contrast metric measurements.

At 218, a scan prescription is selected for the CT imaging system 100 based on the flow rate of the contrast material. The scan prescription may be selected by the processing unit 118 from a range of options that provide a best match. For example, for helical scanning, various gantry rotation speeds, collimations, and pitches may be considered. Optionally, where two or more options are similar in speed, other considerations such as the clinical task or radiation dose efficiency, may also be considered by the system or by the user in making a determination. Axial scanning may possibly also be used, with a system-adjusted scan delay based on the axial to axial scan distance and the measured contrast velocity, but helical scanning is typically recommended.

Figure 8:
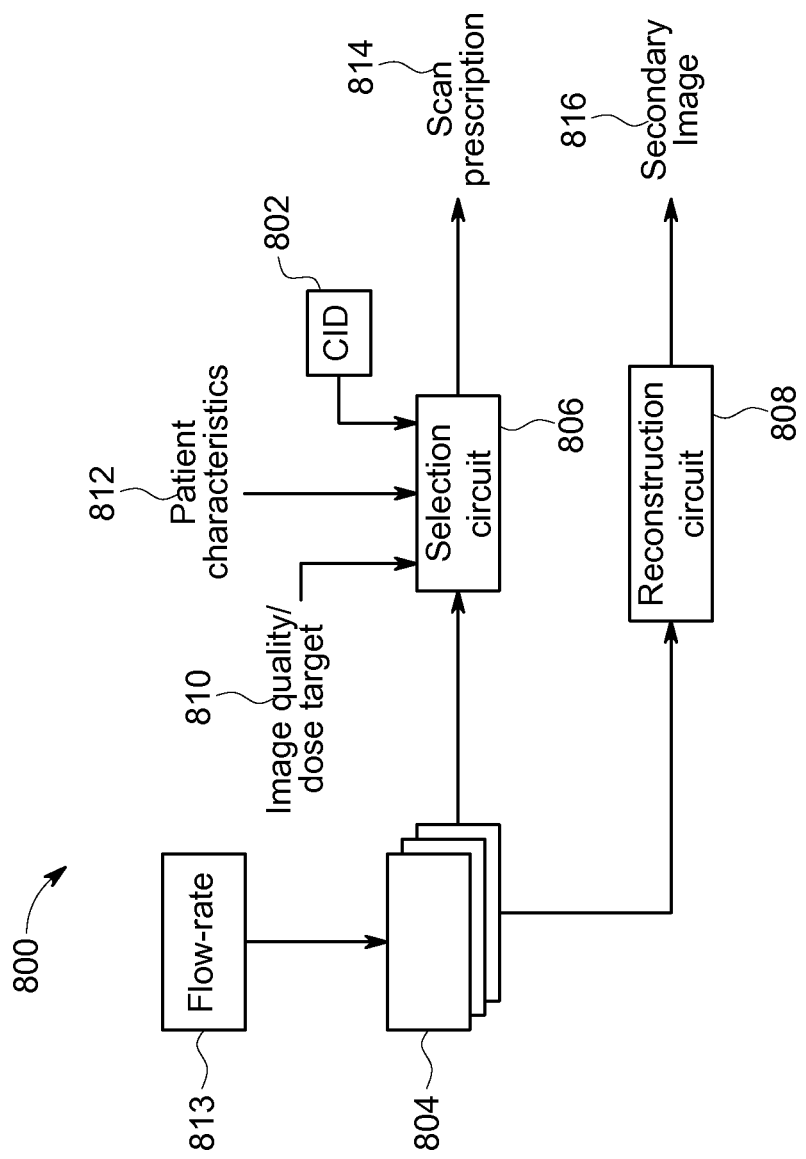
FIG. 8 illustrates a schematic process flow for automatic selection of flow rate compensated acquisition parameters in accordance with various embodiments.

FIG. 8 illustrates a schematic process flow 800 for guided selection of acquisition settings for imaging systems. It may be noted that the various blocks depicted in FIG. 8 may represent process steps in some embodiments and/or components or aspects configured to perform process steps in some embodiments (e.g., the processing unit 118). Generally, as seen in FIG. 8, a selection of acquisition parameters corresponding to a scan prescription are derived from a profile database based on a clinical identifier (CID), one or more patient characteristics, a flow rate of the contrast material, and/or an acquisition condition target (e.g., contrast dosage target, noise index). In various embodiments, certain blocks may be omitted, and/or additional process blocks may be added (see, e.g., FIG. 2).

For the embodiment depicted in FIG. 8, at block 813, the processing unit 118 may calculate the flow rate of the contrast material as described at 212 of FIG. 2.

In the illustrated embodiment, at block 804, the processing unit 118 may determine select scan settings from a plurality of scan settings based on the flow rate of the contrast material. The plurality of scan settings may be provided on a profile database constructed from priori information (e.g., patient population acquisition studies, pre-programmed rule sets) and/or generated from user inputs. Generally, the flow rate provides a "pointer" on relevant acquisition or scan settings from the profile database. For example, processing unit 118 may determine which of the plurality of scan settings may result in potential scan prescriptions having a table feed rate moving at and/or approximate to the calculated flow rate. The plurality of scan settings that result in the potential scan prescriptions may be flagged and/or selected by the processing unit 118 as the select scan settings. Additionally or alternatively, the processing unit 118 may determine the select scan settings based on the flow rate through the ROI 306 and a prep delay (e.g., an amount of time between injection of the contrast material and the start of the scan at the first location 302).

The processing unit 118 may include a selection circuit block 806. The selection circuit block may identify one of the select scan settings provided by at the block 804 as a scan prescription 814 corresponding to the acquisition settings for the resultant medical image. The scan prescription 814 may be identified by the selection circuit block 806 from the select scan settings based on a clinical identifier (CID) 802.

The CID 802 corresponds to a clinical context for the scan. The CID 802 provides one or more scan attributes needed for a resultant medical image. The CID 802 may be received from a user via a user interface (e.g., the user interface 160), received remotely from a patient database, and/or the like. The CID 802 may include an anatomy of interest (e.g., organ of interest, region of interest) of the patient 123 and a clinical indication corresponding to the purpose or objective of the CT scan. The CID 802 may be received by the processing unit 118 from the user interface 160.

The selection circuit block may further identify the scan prescription 814 based on patient characteristics 812 and/or image quality and dose targets 810 received by the user via the user interface. The patient characteristics 812 may be determined from a scout scan.

The selection circuit block 806 may identify which combination of the select scan settings may generate a resultant medical image having scan attributes of the CID 802 and have acquisition conditions the same as and/or more proximate to the targets 810. For example, the select scan settings may include high gantry rotation speeds, helical pitch, and/or high collimation width to achieve as table feed rate that matches the calculated flow rate. The selection circuit block 806 may determine which select scan settings would be appropriate or most optimal based on the CID 802. For example, the CID 802 may provide a scan attribute corresponding to a high plane temporal resolution, which may be associated with a need for a higher gantry rotation sped. Additionally or alternatively, the selection circuit block 806 may further calculate candidate image quality and corresponding doses associated with the select scan settings to determine which of the select scan settings may be proximate to and/or result in a scan having the image quality and dose targets 810. The selection circuit block 806 may further determine which combination of the select scan settings may be affected by the one or more patient characteristics 812, such as reducing the scan attributes in it resultant medical image.

Additionally or alternatively, the processing unit 118 may determine the scan prescription 814 from multiple flow rates determined from more than two locations. For example, as described above, the processing unit 118 may determine first and second flow rates based on first, second, and third contrast metrics. The processing unit 118 may determine an average, flow rate from the first and second flow rates to determine the flow rate 813, which may be used to select the select scan settings utilized by the selection circuit block 806 to determine the scan prescription 814. Additionally or alternatively, the scan prescription 814 may have different acquisition settings based on a position of the FOV of the X-ray source 112 with respect to first location 302, the second location 304, and/or the third location.

For example, the selection circuit block 806 may determine the scan prescription 814 includes different acquisition settings, such as multiple table feed rates (e.g., rate the motorized table 122 of FIG. 1 moves along the z-axis extending through the gantry 110), while scanning from the first location 302 to the third location relative to scanning from the third location to the second location 304. The processing unit 118 may calculate a first flow rate between the first location 302 and the third location and a second flow rate between the third location and the second location 304. The first flow rate may be different than the second flow rate (e.g., faster, slower). Based on the different flow rates, the scan prescription 814 may include a first table feed rate based on the first flow rate and a second table feed rate based on the second flow rate.

The first table feed rate and the second table feed rate may correspond to a position of the patient 123 and/or motorized table 122 with respect to the gantry 110 and/or the FOV of the X-ray source 112. For example, the processing unit 118 may instruct the table motor controller 164 of the acquisition subsystem 142 to move the table at the first table feed rate from the first location 302 to the third location. When the processing unit 118 determines that the third location is positioned within the FOV of the X-ray source 112, the processing unit 118 may instruct the table motor controller 164 to move the motorized table 122 at the second table feed rate.

Returning to FIG. 8, a reconstruction circuit block 808, corresponding to the reconstructor circuit 150, may select one or more reconstruction settings based on the scan attributes provided by the CID 802. The reconstruction settings may include select keV energy level(s), iterative reconstruction (e.g., adaptive statistical reconstruction), direct multi-planar reconstruction, algorithmic reconstruction (e.g., Native VUE®), and/or the like. The select one or more reconstruction settings may be in addition to reconstruction settings selected by the user via the user interface. For example, the reconstruction circuit block 808 may generate a secondary image 816, which may be reconstructed based on the select one or more reconstruction settings, in addition to the resultant medical image, which may be reconstructed based on reconstruction settings selected by the user.

Additionally or alternatively, the scan prescription may include a prep delay. The prep delay may correspond to an amount of time between injection of the contrast material and the start of the scan at the first location 302. The prep delay may be determined by the processing unit 118 from a delay time measured for the first location 302. The delay time may be based on the relative distance to the start of the CT scan (positive or negative) divided by the average velocity or flow rate of the contrast material. The delay time may be further adjusted to account for a difference in the contrast injection duration (typically small for the timing bolus, but longer for a CTA scan), and the initial table acceleration and scanning time for a helical scan before the table is centered on the first location 302, and possibly also with further fixed offsets. Optionally, the pre delay included within the scan prescription may not from the select scan settings. For example, the prep delay may be a predetermined amount of time selected by the user via the user interface 160 or preset before the scan.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "processing unit," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory. EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along, with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
    acquiring image data at a first location of a region of interest (ROI) of a patient over time, the first location located in a field of view (FOV) of a medical imaging system while a contrast material injected into the patient via a bolus injection passes through the first location, wherein the contrast material successively traverses from the first location to a second location of the ROI that is spaced apart from the first location along a length of the ROI;
    analyzing the image data don at the first location to determine a time that a first contrast metric is reached;
    responsive to determining that the first contrast metric is reached, automatically repositioning the patient relative to the FOV of the medical imaging system via a motorized table on which the patient is disposed so that the second location of the ROI is within the FOV of the medical imaging system;
    acquiring image data at the second location of the ROI of the patient over time while the second location of the ROI is within the FOV of the medical imaging system and the contrast material from the bolus injection passes through the second location;
    analyzing the image data at the second location to determine a time that a second contrast metric is reached; and
    calculating a flow rate of the contrast material through the patient based on both a distance between the first location and the second location and a time period between the time that the first contrast metric is reached and the time that the second contrast metric is reached.

2. The method of claim 1, further comprising determining select scan settings from a plurality of scan settings based on the flow rate of the contrast material; and
    performing a clinical scan of the ROI of the patient according to the select scan settings that are determined.

3. The method of claim 1, wherein the image data at the first location includes a plurality of successive contrast values over time, and the image data at the first location is analyzed by comparing contrast values of the plurality of successive contrast values to determine a peak contrast value of the plurality of successive contrast values.

4. The method of claim 1, wherein the second location corresponds to a bifurcated segment of the ROI having first and second branches such that the second contrast metric is based on the contrast material of the first and second branches.

5. The method of claim 1, further comprising:
    calculating a predicted contrast level of the contrast material at a location of the ROI between the first location and the second location based on the flow rate; and
    displaying the predicted contrast level on a display.

6. The method of claim 1, further comprising generating a flow rate report based on the flow rate, and displaying at least a portion of the flow rate report on a display.

7. The method of claim 1, further comprising, comparing the image data at the second location of the ROI with a baseline image, wherein the baseline image corresponds to image data at the second location that is either acquired before the contrast material is injected or after the contrast material is through the second location.

8. The method of claim 1, wherein the medical imaging system is a computed tomography (CT) imaging system, a multi-modality CT and positron emission tomography imaging system, or a multi-modality CT and single photon emission CT imaging system.

9. A medical imaging system comprising:
    an acquisition unit comprising a computed tomography (CT) detector configured to collect imaging data; and
    a processing unit comprising one or more processors operably coupled to the acquisition unit and to a motorized table configured to support a patient, the processing unit configured to:
    receive image data at a first location of a region of interest (ROI) of the patient disposed on the motorized table, wherein the image data is acquired by the acquisition unit over time while the first location is located in a field of view (FOV) of the acquisition unit and while a contrast material injected into the patient via a bolus injection passes through the first location, wherein the contrast material successively traverses from the first location to a second location of the ROI that is spaced apart from the first location along a length of the ROI;
    analyze the image data at the first location to determine a time that a first contrast metric is reached;
    responsive to determining that the first contrast metric is reached, generating a control signal for the motorized table to automatically move relative to the acquisition unit to reposition the patient relative to the FOV so that the second location of the ROI is within the FOV of the acquisition unit;
    acquire image data at the second location of the ROI of the patient over time while the second location of the ROI is within the FOV and the contrast material from the bolus injection passes through the second location;

analyze the image data at the second location to determine a time that a second contrast metric is reached; and calculate a flow rate of the contrast material through the patient based on both a distance between the first location and the second location and a time period between the time that the first contrast metric is reached and the time that the second contrast metric is reached.

10. The medical imaging system of claim 9, wherein the processing unit is further configured to select a scan prescription for the acquisition unit based on the flow rate of the contrast material.

11. The medical imaging system of claim 9, wherein the first contrast metric is reached at the time that an associated Hounsfield unit (HU) value from the image data at the first location exceeds a first predetermined threshold, and the second contrast metric is reached at the time that an associated Hounsfield unit (HU) value from the image data at the second location exceeds a second predetermined threshold.

12. The medical imaging system of claim 9, wherein the image data at the first location includes a plurality of successive contrast values over time, and the image data at the first location is analyzed by comparing contrast values of the plurality of successive contrast values to determine a peak contrast value of the plurality of successive contrast values.

13. The medical imaging system of claim 9, wherein the second location corresponds to a bifurcated segment of the ROI having first and second branches such that the second contrast metric is based on the contrast material of the first and second branches.

14. The medical imaging system 12, further comprising a display, wherein the processing unit is further configured to:
calculate a predicted contrast level of the contrast material at a location of the ROI between the first location and the second location based on the flow rate; and
display the predicted contrast level on the display.

15. A tangible and non-transitory computer readable medium comprising one or more computer software modules configured to direct one or more processors to:
acquire image data at a first location of a region of interest (ROI) of a patient over time, the first location located in a field of view (FOV) of a medical imaging system while a contrast material injected into the patient via a bolus injection passes through the first location, wherein the contrast material successively traverses from the first location to a second location of the ROI that is spaced apart from the first location along a length of the ROI, wherein the image data at the first location includes a first plurality of successive contrast values of the first location over time, each contrast value in the first plurality associated with an amount of the contrast material present at the first location at a different respective time;
analyze the image data at the first location by comparing the contrast values of the first plurality of successive contrast values to determine a time at which a peak contrast value of the first plurality of successive contrast values is reached;

responsive to determining the time at which the peak contrast value of the first plurality of successive contrast values is reached, automatically repositioning the patient relative to the FOV of the medical imaging system via a motorized table on which the patient is disposed so that the second location of the ROI is within the FOV of the medical imaging system;
acquire image data at the second location of the ROI of the patient over time while the second location of the ROI is within the FOV of the medical imaging system and the contrast material from the bolus injection passes through the second location, wherein the image data at the second location includes a second plurality of successive contrast values of the second location over time, each contrast value in the second plurality associated with an amount of the contrast material present at the second location at a different respective time;
analyze the image data at the second location by comparing the contrast values of the second plurality of successive contrast values to determine a time at which a peak contrast value of the second plurality of successive contrast values is reached; and
calculate a flow rate of the contrast material through the patient based on both a distance between the first location and the second location and a time period between the time at which the peak contrast value of the first plurality of successive contrast values is reached and the time at which the peak contrast value of the second plurality of successive contrast values is reached.

16. The method of claim 1, wherein the first location and the second location correspond to a first edge of the ROI and a second edge of the ROI, respectively, which define boundaries of the ROI of the patient along a Z-axis.

17. The method of claim 1, wherein the image data at the first location of the ROI that is acquired over time includes a plurality of successive contrast values acquired at different times,
wherein the first contrast metric corresponds to a peak contrast value, and the time that the first contrast metric is reached is the time at which the peak contrast value of the plurality of successive contrast values is acquired.

18. The method of claim 1, further comprising automatically determining the first location of the ROI and the second location of the ROI based on a clinical identification of the ROI and patient characteristics of the patient.

19. The medical imaging system of claim 9, wherein the processing unit is further configured to determine select scan settings from a plurality of scan settings based on the flow rate of the contrast material, and perform a clinical scan of the ROI of the patient according to the select scan settings that are determined.

20. The medical imaging system of claim 9, wherein the processing unit is further configured to automatically determine the first location of the ROI and the second location of the ROI based on a clinical identification of the ROI and patient characteristics of the patient.

* * * * *